(12) United States Patent
Liang et al.

(10) Patent No.: US 11,782,942 B2
(45) Date of Patent: Oct. 10, 2023

(54) AUTO-GENERATING GROUND TRUTH ON CLINICAL TEXT BY LEVERAGING STRUCTURED ELECTRONIC HEALTH RECORD DATA

(71) Applicant: International Business Machines Corporation, Armonk, NY (US)

(72) Inventors: Jennifer J Liang, New York, NY (US); Diwakar Mahajan, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 669 days.

(21) Appl. No.: 16/814,896

(22) Filed: Mar. 10, 2020

(65) Prior Publication Data

US 2021/0286821 A1   Sep. 16, 2021

(51) Int. Cl.
*G06F 16/25* (2019.01)
*G16H 10/60* (2018.01)
*G06F 16/332* (2019.01)
*G06F 16/242* (2019.01)
*G06N 20/00* (2019.01)
(Continued)

(52) U.S. Cl.
CPC ............ *G06F 16/25* (2019.01); *G06F 16/243* (2019.01); *G06F 16/3329* (2019.01); *G06F 16/383* (2019.01); *G06F 40/295* (2020.01); *G06F 40/30* (2020.01); *G06F 40/40* (2020.01); *G06N 20/00* (2019.01); *G16H 10/60* (2018.01)

(58) Field of Classification Search
None
See application file for complete search history.

(56) References Cited

U.S. PATENT DOCUMENTS

2007/0185739 A1 *   8/2007   Ober ...................... G16H 50/20
                                                     600/301
2017/0193185 A1 *   7/2017   Barker .................. G06F 16/334
(Continued)

OTHER PUBLICATIONS

Liang et al., A novel system for extractive clinical note summarization using EHR data, Proc. 2nd Clinical Natural Language Processing Workshop. Minneapolis, Minnesota, pp. 46-54, Jun. 7, 2019.
(Continued)

*Primary Examiner* — Thu N Nguyen
(74) *Attorney, Agent, or Firm* — Kristofer Haggerty; Otterstedt & Kammer PLLC

(57) ABSTRACT

A method improves performance of natural language processing by automatically generating ground truth from electronic health records comprising unstructured clinical notes and structured data comprising entries each having respective values for fields. The method includes: linking a given one of the notes to a given one of the entries responsive to determining that a specified field within the given entry matches an item of metadata for the given note; determining an initial set of the notes which satisfy criteria selected such that the criteria are a proxy for the ground truth, wherein the given note is determined to satisfy the criteria based at least in part on the given entry linked thereto; and designating at least a portion of the initial set of notes which satisfy the criteria, and the entries linked to the portion of the initial set of notes which satisfy the criteria, as the ground truth.

21 Claims, 3 Drawing Sheets

(51) Int. Cl.
*G06F 40/30* (2020.01)
*G06F 40/295* (2020.01)
*G06F 40/40* (2020.01)
*G06F 16/383* (2019.01)

(56) References Cited

U.S. PATENT DOCUMENTS

| | | |
|---|---|---|
| 2018/0089383 A1 | 3/2018 | Allen et al. |
| 2018/0121603 A1 | 5/2018 | Devarakonda et al. |
| 2018/0137433 A1 | 5/2018 | Devarakonda et al. |
| 2018/0196920 A1 | 7/2018 | Liang et al. |
| 2018/0365588 A1 | 12/2018 | Gu et al. |
| 2020/0020011 A1* | 1/2020 | Harvill ............... G06Q 30/0641 |
| 2020/0303072 A1* | 9/2020 | Drokin ................. G16H 10/60 |

OTHER PUBLICATIONS

Poddar et al., Training Models to Extract Treatment Plans from Clinical Notes Using Contents of Sections with Headings, Submitted on Jun. 27, 2019, https://arxiv.org/abs/1906.11930, 15 pages.

Liang et al., Ground Truth Creation for Complex Clinical NLP Tasks—an Iterative Vetting Approach and Lessons Learned. AMIA Joint Summits on Translational Science proceedings. AMIA Joint Summits on Translational Science, vol. 2017, pp. 203-212. Jul. 26, 2017.

Apampari et al., emrQA: A Large Corpus for Question Answering on Electronic Medical Records, Submitted on Sep. 3, 2018, https://arxiv.org/abs/1809.00732, 12 pages.

* cited by examiner

FIG. 2
200

280 Native Structured Data Elements

290 Derived Insights

| 281 Patient ID | 282 Encounter ID | 283 Medicine | 284 Strength | 285 Form | 286 Instructions (sig) | 287 Start Date | 288 End Date | 291 DAILY DOSE | 292 MEDICATION CHANGE |
|---|---|---|---|---|---|---|---|---|---|
| 12345 | 11111111 | Atenolol | 50 mg | tablet | Take one and a half tabs twice a day | 2011-05-24 | 2011-06-09 | 150 MG | START |
| 12345 | 22222222 | Atenolol | 50 mg | tablet | Take one and a half tabs twice a day | 2011-06-09 | 2011-10-12 | 150 MG | NO CHANGE |
| 12345 | 33333333 | Atenolol | 50 mg | tablet | Take 100 mg by mouth twice daily | 2011-10-12 | 2012-03-27 | 200 MG | INCREASE |
| 12345 | 44444444 | Atenolol | 100 mg | tablet | Take 1 tablet by mouth twice daily | 2012-03-27 | 2012-07-09 | 200 MG | NO CHANGE |

FIG. 3
300

380 Native Structured Data Elements

390 Derived Insights

| 381 Patient ID | 382 Encounter ID | 383 Date Time | 384 Analyte | 385 Value | 386 UOM | 391 ABNORMAL FLAG | 392 DELTA | 393 BASELINE MEAN | 394 BASELINE NADIR | 395 BASELINE RECENT |
|---|---|---|---|---|---|---|---|---|---|---|
| 12345 | 12121212 | 2011-10-27 19:29:00 | creatinine | 1.03 | mg/dL | NORMAL | N/A | 1.03 | 1.03 | N/A |
| 12345 | 13131313 | 2012-03-21 20:14:00 | creatinine | 0.89 | mg/dL | NORMAL | -0.14 | 0.96 | 0.89 | 1.03 |
| 12345 | 14141414 | 2012-07-24 15:00:00 | creatinine | 2.01 | mg/dL | ABNORMAL | 1.12 | 1.31 | 0.89 | 0.89 |
| 12345 | 15151515 | 2012-07-29 20:12:00 | creatinine | 1.02 | mg/dL | NORMAL | -0.99 | 1.24 | 0.89 | 2.01 |
| 12345 | 16161616 | 2013-03-06 17:10:00 | creatinine | 1.45 | mg/dL | ABNORMAL | 0.43 | 1.28 | 0.89 | 1.02 |
| 12345 | 17171717 | 2013-07-15 22:36:00 | creatinine | 1.54 | mg/dL | ABNORMAL | 0.09 | 1.32 | 0.89 | 1.45 |

900

AUTO-GENERATING GROUND TRUTH ON CLINICAL TEXT BY LEVERAGING STRUCTURED ELECTRONIC HEALTH RECORD DATA

BACKGROUND

The present invention relates to the electrical, electronic and computer arts, and, more particularly, to improvements in natural language processing of electronic health records.

The patient electronic health record (EHR) usually includes both structured and unstructured data. Structured EHR data typically uses a controlled vocabulary and have an organized format allowing for easier processing, and includes information such as problem list, medication list, allergies, vital signs, lab results, ordered procedures, etc. Unstructured EHR data, or clinical text, do not follow a particular format and are therefore more difficult for a system to understand, but have the benefit of allowing clinicians to document more nuanced or contextual information to paint a more complete picture of the patient's health. Some examples of clinical notes within EHR data are physician progress notes, nursing notes, discharge summaries, diagnostic test reports, correspondence, patient emails, etc.

Clinical notes within patient electronic health records (EHRs) are traditionally a rich source of data where detailed information about the patient's medical history and clinical care process is documented. Some of this information is not captured anywhere else within the EHR. but could potentially have great impact on the patient care process. Some examples include: reasoning behind medical decision-making (e.g. why did the doctor decide on treatment A vs treatment B?), medication changes (e.g. instructions to hold BP meds for a few days), adverse drug reactions (e.g. patient experiencing diarrhea on higher dose of metformin), social determinants of health (e.g. patient has limited access to a car which has resulted in multiple missed appointments), patient adherence (e.g. is patient taking medication as prescribed?), patient preferences (e.g. patient does not like needles).

However, physicians at the point of care are mostly unable to review much of this unstructured information due to the abundance of notes within the patient EHR and the time constraint inherent in the clinical setting. Advances in natural language processing (NLP) and machine learning techniques in recent years within the medical/clinical domain have shown promise in effectively analyzing EHR data with potential applications in patient care, clinical research, hospital operations management, etc.

A significant barrier in effectively utilizing machine learning techniques on clinical data is the need for a sufficiently large "ground truth" data set to train and test the models. This is because manual annotation to generate labeled data on clinical notes is a time-consuming and tedious process requiring human annotators with domain expertise. The current "gold standard" process for ground truth generation on clinical text is a manual process that requires medical experts to manually review hundreds or thousands of notes. This process is time-consuming, requires trained individuals, and is subject to human error. Current techniques require employing subject matter experts (SME), which are expensive annotation resources, who must abide by access restrictions regarding protected health information (PHI), such as the Health Insurance Portability and Accountability Act (HIPAA). Thus, automated generation of annotations for information extraction on clinical text remains a long-felt but unmet need.

SUMMARY

An illustrative embodiment includes a method for improving performance of a natural language processing task by automating generation of ground truth from electronic health records. The electronic health records comprising unstructured clinical notes and at least one table of structured data comprising entries each having respective values for one or more fields. The method includes linking at least a given one of the unstructured clinical notes to at least a given one of the structured data entries responsive to determining that a value for a specified field within the given one of the structured data entries matches an item of metadata for the given one of the unstructured clinical notes, and determining an initial set of the unstructured clinical notes which satisfy one or more criteria. The one or more criteria selected such that the one or more criteria are a proxy for the ground truth, and the given one of the unstructured clinical notes is determined to satisfy the criteria based at least in part on the given one of the structured data entries linked thereto. The method also includes designating at least a portion of the initial set of unstructured clinical notes which satisfy the criteria, and the structured data entries linked to the portion of the initial set of unstructured clinical notes which satisfy the criteria, as the ground truth.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Illustrative embodiments of the present invention have practical applications and provide technological improvements. For example, an illustrative embodiment of the proposed invention can automatically generate "silver standard" ground truth for a variety of clinical NLP tasks without requiring any preexisting ground truth, such as initial manually created "gold standard" ground truth. Illustrative embodiments of the present invention provide a much faster and scalable process for auto-generating "silver standard" ground truth adaptable to a multitude of information extraction tasks with much less expert input than conventional approaches, thus permitting faster, less labor-intensive creation of ground truth. An illustrative embodiment of the present invention provides a solution for reducing expert input needed to scale to annotate a larger dataset. These and other features and advantages of the present invention will become apparent from the following detailed description of illustrative embodiments thereof, which is to be read in connection with the accompanying drawings.

BRIEF DESCRIPTION OF THE DRAWINGS

FIG. 2 shows exemplary structured medication order data in accordance with an illustrative embodiment of the present invention;

FIG. 3 shows exemplary structured lab test result data 300 in accordance with an illustrative embodiment of the present invention;

DETAILED DESCRIPTION

Illustrative embodiments of the present invention address the problematic lack of annotations for information extraction on clinical text. As discussed above, the current process for ground truth generation on clinical text ("gold standard") is a manual process that is time-consuming, requires trained individuals, and is subject to human error. Conversely, illustrative embodiments of the present invention can auto-generate ground truth ("silver standard") for information extraction from clinical text using structured EHR data. Illustrative embodiments of the proposed invention can potentially generate ground truth for a variety of clinical NLP tasks without requiring any preexisting ground truth. Illustrative embodiments of the present invention provide a much faster and scalable process for auto-generating "silver standard" ground truth adaptable to a multitude of information extraction tasks with much less expert input needed. As used herein, "gold standard" ground truth refers to manually labeling data by a human expert, while "silver standard" ground truth refers to labels automatically generated from the data itself.

Figure 1:
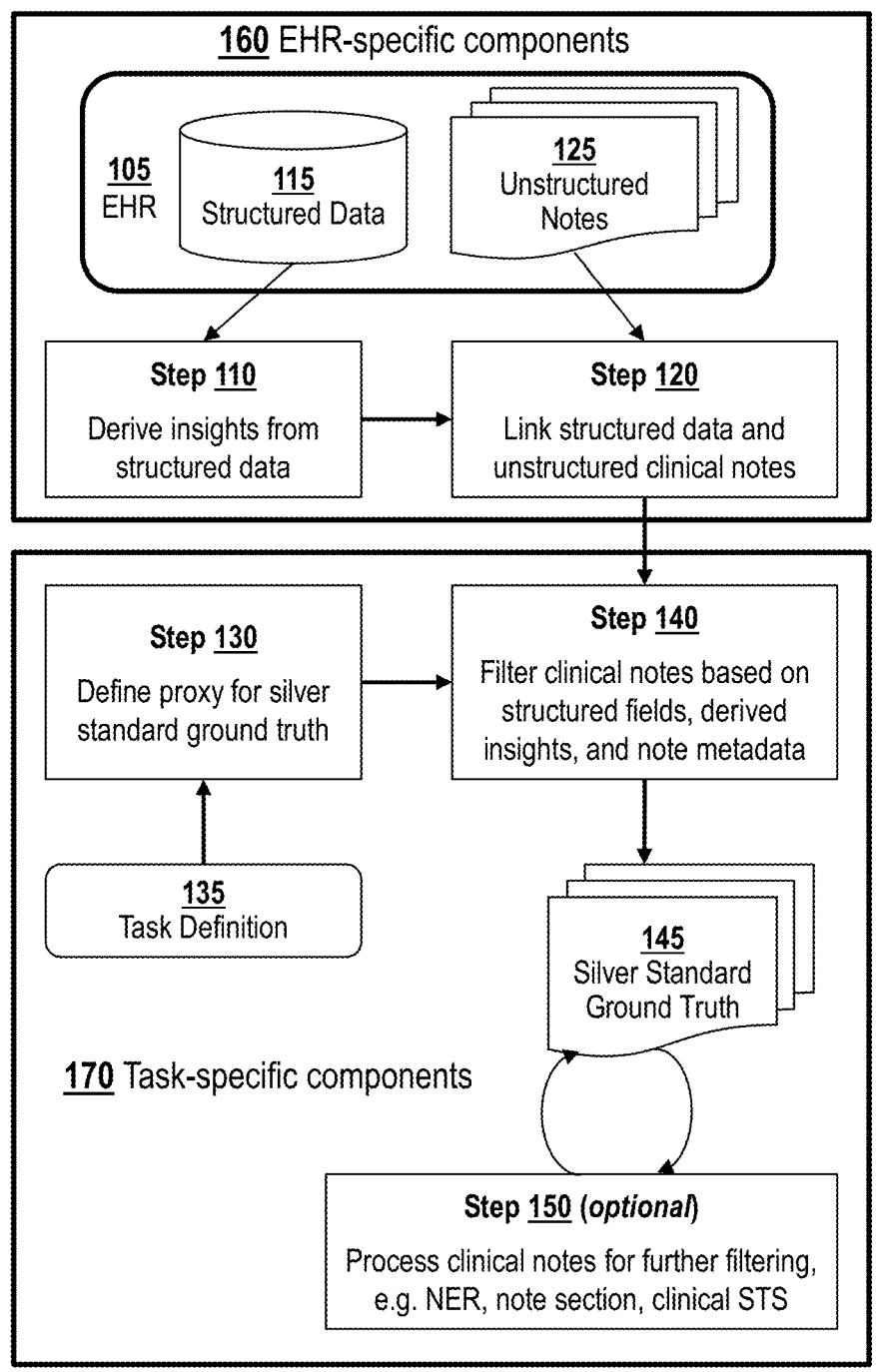
FIG. 1 is a combined block/flow diagram depicting one or more aspects of an illustrative embodiment of the present invention.

FIG. 1 is a combined block/flow diagram depicting one or more aspects of an illustrative embodiment of the present invention. Electronic health records (EHR) 105 typically includes structured data 115 and unstructured notes 125. Structured EHR data 115 is organized into various tables that each have a set of fields. An illustrative embodiment 100 may begin with step 110 involves extracting derived insights from structured EHR entries 115. Depending on the type of structured data, the data format, and the availability of various fields, different processing steps may be implemented to extract various kinds of derived insights.

FIG. 2 shows exemplary structured medication order data in accordance with an illustrative embodiment of the present invention. Medication order data 200 may represent a portion of the structured EHR data 115 following execution of step 110 in FIG. 1. Structured medication order data 200 includes native structured data elements 280 existing in 115 prior to step 110, as well as derived insights 290 created from native elements 280 in step 110. Thus, each entry of medication order data 200 may include native structured data elements 280 representing a patient identifier 281, an encounter (e.g., outpatient appointment or inpatient hospitalization) identifier 282, medication name 283, strength 284, form or formulation 285, instructions (sig) 286, start date 287, and end date 288.

From these native structured data elements 280, additional derived insights 290 can be obtained in step 110. The derived insights 290 for each entry within medication order data 200 may include daily dosage 291 (dosage of medication prescribed over a single day) or medication change 292: e.g., if this entry represents a new medication, a refill of an existing medication with no change in daily dose (even with a different strength—e.g., two 50 mg tablets rather than one 100 mg tablet), or a change in daily dose: increase or decrease. In the example shown in FIG. 2, the processing to derive daily dosage 291 from the native elements 280 may include parsing, for example, the strength field 284 (e.g., "50 mg") and the instruction field 286 (e.g., "take two tablets twice daily"). Processing to extract medication change status 292 as a derived insight 290 may require combining the medication name 283, the start date 287, and the end date 288 originally provided 280 in the structured data 115, and the previously-derived daily dosage 291. If there are inconsistencies and/or unreliable data (e.g., variations in the medication name 283 because of different brand names or generic names), step 110 may include retrieving and/or normalizing the necessary information by linking the structured medication order 200 to an external resource such as RxNorm using either the medication name field 281 or a code, such as National Drug Code (NDC), if provided.

FIG. 3 shows exemplary structured lab test result data 300 in accordance with an illustrative embodiment of the present invention. Lab test result data 300 may represent a portion of the structured EHR data 115 following execution of step 110 in FIG. 1. Structured lab test result data 300 includes native structured data elements 380 existing in 115 prior to step 110, as well as derived insights 390 created from native elements 380 in step 110. Thus, each entry of lab test results data 300 may include native structured data elements 380 representing a patient identifier 381, an encounter (e.g., outpatient appointment or inpatient hospitalization) identifier 382, date and time the test was ordered 383, the name of the test analyte 384, the measured value of the analyte for the test 385, and the corresponding unit of measurement (UOM) 386.

Derived insights 390 may include a flag indicating whether the value is within a normal range, the patient's baseline for a particular lab test (i.e. the patient's "normal" or "usual" measurement of a lab analyte), or change from previous lab result (i.e. the delta between a specific lab result and the previous result for the same lab). The baseline value for a specific lab can be estimated in a number of ways. Some proposed estimations are: (1) the mean outpatient value, (2) the most recent outpatient value, (3) the nadir outpatient value, and (4) the most recent inpatient or outpatient value. Also, depending on the type of lab, additional baseline estimations can be applied. For example, the Modification of Diet in Renal Disease (MORD) equation (back-estimation) can be used for estimating baseline for serum creatinine. All of these methods for baseline estimation can be used as part of the processing of structured lab data, each becoming a unique derived insight. In FIG. 3, the derived insights include the aforementioned flag 391 indicating whether the value is within a normal range, the change from the immediately preceding value (delta) 392, the running average (baseline: mean) 393, the lowest value (baseline: nadir) 394, and the immediately preceding value (baseline: prior) 395.

Returning to FIG. 1, step 120 involves linking the structured EHR entries 115 (including both the native fields 280/380 and the derived insights 290/390 from step 110) to unstructured clinical notes 125. For example, it may be desirable to link structured EHR entries 115 and clinical notes 125 generated from the same encounter (e.g., outpatient office visit or inpatient facility stay).

This linkage can occur in multiple ways depending on the availability of various fields within the EHR data 105 (including 115 and 125). Usually there is an ID that groups together data elements originating from the same patient encounter (e.g., 282 and 382 in FIGS. 2 and 3, respectively). The existence and naming of this ID differs depending on the specific EHR system and format. For outpatient visits, there may be an ENCOUNTER ID that represents everything that happened for a single patient visit. In the case of inpatient stays, you may have an ADMISSION_ID which represents a single patient admission to the hospital, and/or an ICUSTAY_ID to specifically identify patient stays in the intensive care unit (ICU). In the absence of an ID to link together structured and unstructured EHR data elements, secondary methods of linkage can be leveraged such as: (a) the dates when events were generated (e.g. a medication order date in structured medications data 115/280 may be linked to note date in note metadata 125), (b) the authorizing provider who initiated the events (e.g. provider who ordered lab in structured lab results 115/380 may be linked to note author in note metadata), or (c) the department where events originated from, etc.

The resulting output is an expanded representation of the patient EHR 105 where each structured entry 115 (from step 110) contains both native data elements (280/380) and derived insights (290/390) and also (from step 120) is linked to unstructured clinical notes 125 generated from the same encounter along with the associated note metadata (e.g., note type, note data, note author, etc.) Accordingly, the unstructured notes 125 (with associated metadata) for a given patient may be linked to the structured data 115, including both native elements 280/380 as well as derived insights 290/390.

Note that steps 110 (extracting derived insights) and 120 (linking to unstructured notes) can be a pre-processing step run on all EHR data 105 prior to deciding on a specific use case or information extraction task 135. Thus, steps 110 and 120 may be specific to EHR 105 (e.g., dependent on the particular content and/or format of EHR 105) as indicated by 160, while steps 130-150 may be specific to task 135 (e.g., dependent on the particular use case or information extraction task) as indicated by 170. Similar to the manner in which steps 110 and 120 were described with reference to examples of structured data 115 shown in FIGS. 2 and 3, the remaining steps 130-150 will be discussed with reference to two sample use cases 135: Sample Task "A" is to extract medication change events from clinical notes, while Sample Task "B" is to identify decline in heart failure from clinical notes.

Step 130 defines a proxy for silver standard ground truth based on the particular use case or task definition 135. This involves using the task definition 135 to determine appropriate values for EHR structured elements (115/280/380), derived insights (290/390), and note metadata (125) to serve as a proxy for the silver standard ground truth 145. Step 130 is the only step in FIG. 1 which may require from a domain expert to guide what structured data sources and types of notes are most pertinent.

Where task 135 is the aforementioned "A" (to extract medication change events from clinical notes), step 130 may determine criteria suitable as a proxy for ground truth to be clinical notes 125 linked to structured medication entries 200 where derived medication change insight 292 is START, STOP, INCREASE, or DECREASE. Where task 135 is the aforementioned "B" (to identify decline in heart failure from clinical notes), step 130 may determine criteria suitable as a proxy for ground truth to be clinical notes 135 with Note Author Type=Physician and Encounter Diagnosis Code=428.* that are linked to either (1) a structured lab 300 of type 384 BNP (brain natriuretic peptide) determined to be abnormal in derived insight 391 or (2) a structured medication 200 with generic name 283 FUROSEMIDE that has derived medication change insight 292 START or INCREASE.

Step 140 involves application of the proxy (e.g., criteria) defined in step 130 to the output of step 120. Depending on the specific use case 135 and ground truth needed (e.g., medication change, disease status), the patient records (e.g., clinical notes 125) are filtered using a combination of note metadata 125, native attributes 280/380 and derived insights 290/390 from linked structured entries 115. The resulting output 145 is a smaller set of clinical notes with associated metadata 125 and linked structural data 115 that satisfies the proxy definition 130 specific to the task at hand 135. This output 145 may be directly used as "silver standard" ground truth for the specified task 135, such as in analytic training and development.

Step 150 includes optional post-processing (e.g., further filtering of clinical notes) to achieve improved quality (e.g. "cleaner") ground truth 145 prior to use, e.g., in analytic training and development. Step 150 may include applying natural language processing (NLP) to clinical text to extract information which can be leveraged to discard selected clinical notes of lower quality. Examples of processes which can be used, in isolation or in any combination, to provide further filtering mechanisms to improve the quality of selected clinical notes for silver ground truth 145 include but are not limited to:

1) Named Entity Recognition (NER): A pretrained model on NER task can be employed to identify various entities present in the natural language of clinical text (e.g. medication names, disease names). These identified entities can then be used to further filter selected notes.

2) Note Section Classification: A pretrained model (learned or rule-based or hybrid) can be employed to identify whether a sentence belongs to a specific note section (e.g. Assessment & Plan (AP), Medication Section, Past Medical History (PMH)) in the clinical notes. Given the certain attributes of a note section (e.g. PMH is usually about past events etc.), the selected notes can be filtered to further improve the quality of the silver ground truth.

3) Clinical Semantic Textual Similarity (STS): Sentences from various notes can be compared to derive semantic similarity between them. For example, sentences "Lisinopril was dispensed" & "The patient is on lisinopril" have high semantic similarity. This measure can be used to identify repetitive information within a note and between notes. This can help identify high veracity sentences which have a higher probability of recording the required insight.

By way of example, for the aforementioned Sample Task "A" (extract medication change events from clinical notes), one can first employ a NER extraction-based mechanism to identify medication names in the clinical text. This is based on the fact that clinical notes explicitly mentioning the medication have a higher chance of containing the ground truth for the particular medication change insight. In other words, if the medication in the medication change derived insight is also present in the clinical text of the linked note, retain this note as ground truth, and discard all other ground truth values not meeting this criterion.

One could then restrict these medication mentions in clinical notes to only those appearing in certain sections of the note using a pretrained model for note section classification. For example, the History of Present Illness (HPI) and Assessment/Plan (AP) sections of the note typically contain information most relevant to the current visit, while the Past Medical History (PMH) section is usually about past events. Therefore for this task, further restrict the silver ground truth to be only those notes where the mention of the medication name (from NER task) is present either in HPI or AP sections.

As another example, for the aforementioned Sample Task "B" (identify decline in heart failure disease status from clinical notes) one can first employ a NER extraction-based mechanism to identify mentions (and variants) of the disease "heart failure", the medication "furosemide" or the lab "BNP" in the clinical text. Absence of these specific concepts in the clinical note can be used to discard notes which are less likely to contain information relevant to this specific task. Restricting to only notes with mentions of "heart failure", "furosemide" or "BNP" ensures that the disease of interest was actually discussed during the specific encounter and note. One could also further restrict the silver ground truth to be only those notes where the mention of interest (from NER task) is present in the AP section (from Note Section Classification model).

Illustrative embodiments of the present invention provide a novel methodology of auto-generating silver standard ground truth for various information extraction tasks on unstructured clinical notes. Illustrative embodiments of the present invention provide a much faster and scalable process for auto-generating "silver standard" ground truth adaptable to a multitude of information extraction tasks with much less expert input needed than current approaches, thus permitting faster, less labor-intensive creation of ground truth. Illustrative embodiments include a novel methodology for identifying and automatically extracting ground truth leveraging the unique way EHR systems organize their structured and unstructured information, with particular utility in clinical NLP. Illustrative embodiments can leverage derived insights from structured EHR entries and linkages between structured and unstructured elements within the EHR to identify clinical notes of interest. Illustrative embodiments may also filter unstructured data based on the combined metadata obtained from structured and unstructured elements within the EHR to improve the quality of silver standard ground truth.

An illustrative embodiment of the present invention processes structured EHR data to derive insights, defines a silver ground truth proxy using both native and derived structured EHR elements, leverages linkages between structured and unstructured data to identify notes of interest, and autogenerates a set of notes as silver ground truth. Instead of focusing on a single task like question answering, an illustrative embodiment can adapt to a multitude of information extraction tasks in clinical notes. Thus, an illustrative embodiment can automatically generate "silver standard" ground truth for a variety of clinical NLP tasks without requiring any preexisting ground truth, e.g., initial manually created "gold standard" ground truth. An illustrative embodiment of the present invention provides a solution for reducing expert input needed to scale to annotate a larger dataset. Thus, an illustrative embodiment provides an automated way to generate a large silver standard ground truth by leveraging structured EHR data.

To recapitulate, an illustrative embodiment of the present invention may include a method for auto-generating silver standard ground truth for information extraction from clinical text using structured EHR data. This method may include extracting derived insights from structured EHR entries, and linking structured EHR entries to unstructured clinical notes. The method may also include defining criteria (e.g., values of EHR structured data, derived insights, and note metadata) as a proxy for silver ground truth, and filtering clinical notes based on these criteria. The method may optionally include further filtering of the clinical notes to achieve "cleaner" ground truth.

An illustrative embodiment of the present invention may additionally or alternatively include a method for identifying and extracting ground truth, which includes: deriving one or more insights from one or more structured data within an electronic health record; linking (associating) the one or more structured data and the one or more insights with one or more unstructured clinical notes within the electronic health record; receiving one or more filters to the associated one or more structured data, the one or more insights, and the one or more unstructured clinical notes; and filtering the one or more structured data, the one or more insights, and the one or more unstructured clinical notes. The method may also include processing the filtered one or more structured clinical notes, the one or more insights, and the one or more unstructured clinical notes based on applying at least one of named entity recognition, note section classification, and clinical semantic textual similarity. Linking the structured data with the one or more unstructured clinical notes may be based on one or more of: an ID that groups data elements originating from a same patient encounter, a date on which an event within the electronic health record is generated, an authorizing provider who initialed an event within the electronic health record, or a department from which an event within the electronic health record originates.

One or more embodiments of the invention, or elements thereof, can be implemented, at least in part, in the form of an apparatus including a memory and at least one processor that is coupled to the memory and operative to perform exemplary method steps.

Figure 4:
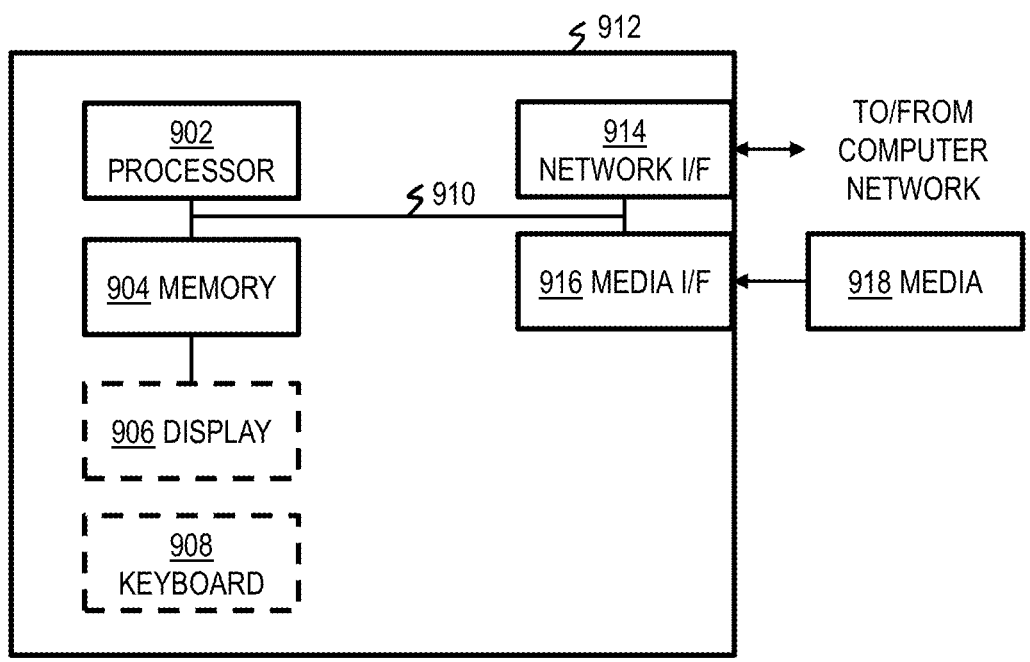
FIG. 4 shows a computer system that may be useful in implementing one or more aspects and/or elements of the invention.

One or more embodiments can make use of software running on a general purpose computer or workstation. With reference to FIG. 4, such an implementation might employ, for example, a processor 902, a memory 904, and an input/output interface formed, for example, by a display 906 and a keyboard 908. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit (for example, printer). The processor 902, memory 904, and input/output interface such as display 906 and keyboard 908 can be interconnected, for example, via bus 910 as part of a data processing unit 912. Suitable interconnections, for example via bus 910, can also be provided to a network interface 914, such as a network card, which can be provided to interface with a computer network, and to a media interface 916, such as a diskette or CD-ROM drive, which can be provided to interface with media 918.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 902 coupled directly or indirectly to memory elements 904 through a system bus 910. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 908, displays 906, pointing devices, and the like) can be coupled to the system either directly (such as via bus 910) or through intervening I/O controllers (omitted for clarity).

Network adapters such as network interface 914 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 912 as shown in FIG. 9) running a server program. It will be understood that such a physical server may or may not include a display and keyboard.

It should be noted that any of the methods described herein can include an additional step of providing a system comprising distinct software modules embodied on a computer readable storage medium; the modules can include, for example, any or all of the elements depicted in the block diagrams or other figures and/or described herein. The method steps can then be carried out using the distinct software modules and/or sub-modules of the system, as described above, executing on one or more hardware processors 902. Further, a computer program product can include a computer-readable storage medium with code adapted to be implemented to carry out one or more method steps described herein, including the provision of the system with the distinct software modules.

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for improving performance of a natural language processing task by automating generation of ground truth from electronic health records, the electronic health records comprising unstructured clinical notes and at least one table of structured data comprising entries each having respective values for one or more fields, the method comprising steps of:

determining an initial set of the unstructured clinical notes which satisfy one or more criteria, wherein the one or more criteria selected such that the one or more criteria are a proxy for the ground truth, and wherein the given one of the unstructured clinical notes is determined to satisfy the criteria based at least in part on the given one of the structured data entries linked thereto;

designating at least a portion of the initial set of unstructured clinical notes which satisfy the criteria as a first component of the ground truth, and designating the structured data entries linked to the portion of the initial set of unstructured clinical notes which satisfy the criteria as a second component of the ground truth in response to the determination of the initial set of the unstructured clinical notes that satisfy the one or more criteria;

using the designated ground truth to train a machine learning model; and using the trained machine learning model to perform the natural language processing task.

2. The method of claim 1, wherein each entry of a given table of the structured data comprises respective values for a predefined set of fields, and wherein the method further comprises adding at least one additional field to each entry of the given table of the structured data, wherein each value for the at least one additional field is derived from at least a portion of the respective values for the predefined set of fields.

3. The method of claim 2, wherein the linking step is responsive to determining that a value for an additional field within the given one of the structured data entries matches an item of metadata for the given one of the unstructured clinical notes.

4. The method of claim 2, wherein the given one of the unstructured clinical notes is determined to satisfy the criteria based at least in part on the additional field within the given one of the structured data entries linked thereto.

5. The method of claim 2, wherein a value for the additional field for a given entry of the table indicates a difference between a value for a predefined field of the given entry and a value for the predefined field of an immediately preceding entry of the table.

6. The method of claim 2, wherein a value for the additional field for a given entry of the table indicates a baseline value for a predefined field of the given entry.

7. The method of claim 6, wherein the baseline value is based at least in part on values for the predefined field of one or more preceding entries of the table.

8. The method of claim 6, wherein the baseline value is based at least in part on an average of the values for the predefined field of the one or more preceding entries of the table.

9. The method of claim 6, wherein a value for the additional field for a given entry of the table indicates whether a value for a predefined field of the given entry is within a specified range.

10. The method of claim 1, wherein the matching value and item of metadata uniquely identifies a patient.

11. The method of claim 1, wherein the matching value and item of metadata uniquely identifies an encounter, outpatient visit, or inpatient stay.

12. The method of claim 1, wherein the matching value and item of metadata identifies a date of service.

13. The method of claim 1, wherein the matching value and item of metadata identifies a treating provider, office, practice, department, or facility.

14. The method of claim 1, wherein using at least a portion of the initial set of unstructured clinical notes which satisfy the criteria, and the structured data entries linked to the portion of the initial set of unstructured clinical notes which satisfy the criteria, as the ground truth for the natural language processing task comprises:
   extracting a subset of the initial set of unstructured clinical notes; and
   designating the subset of the initial set of unstructured clinical notes, and the structured data entries linked to the subset of the initial set of unstructured clinical notes, as the ground truth.

15. The method of claim 14, wherein extracting the subset utilizes at least one of named entity recognition, note section classification, and semantic textual similarity.

16. The method of claim 14, wherein a given one of the notes within the subset is extracted responsive to presence of a specified concept or variant thereof within an assessment/plan (A/P) or history of present illness (HPI) section of the given one of the notes.

17. The method of claim 1, wherein the method does not require manual generation of at least an initial portion of the ground truth.

18. The method of claim 1, wherein the linking is independent of the natural language processing task, and wherein the criteria are selected based at least in part on the natural language processing task.

19. The method of claim 1, further comprising the steps of:
   determining an appropriate medical treatment for at least one patient based at least in part on the at least the natural language processing task; and
   administering the appropriate treatment to the at least one patient.

20. An apparatus for improving performance of a natural language processing task by automating generation of ground truth from electronic health records, the electronic health records comprising unstructured clinical notes and at least one table of structured data comprising entries each having respective values for one or more fields, the apparatus comprising:
   a memory; and
   a processor coupled to the memory, the processor being operative:
      to link at least a given one of the unstructured clinical notes to at least a given one of the structured data entries responsive to determining that a value for a specified field within the given one of the structured data entries matches an item of metadata for the given one of the unstructured clinical notes;
      to determine an initial set of the unstructured clinical notes which satisfy the criteria, wherein the one or more criteria selected such that the one or more criteria are a proxy for the ground truth, and wherein the given one of the unstructured clinical notes is determined to satisfy the criteria based at least in part on the given one of the structured data entries linked thereto;
      to designate at least a portion of the initial set of unstructured clinical notes which satisfy the criteria as a first component of the ground truth, and designating the structured data entries linked to the portion of the initial set of unstructured clinical notes which satisfy the criteria as a second component of the ground truth in response to the determination of the initial set of the unstructured clinical notes that satisfy the one or more criteria;
      using the designated ground truth to train a machine learning model; and
      using the trained machine learning model to perform the natural language processing task.

21. A computer program product for improving performance of a natural language processing task by automating generation of ground truth from electronic health records, the electronic health records comprising unstructured clinical notes and at least one table of structured data comprising entries each having respective values for one or more fields, the computer program product comprising a non-transitory machine-readable storage medium having machine-readable program code embodied therewith, said machine-readable program code comprising machine-readable program code configured:
   to link at least a given one of the unstructured clinical notes to at least a given one of the structured data entries responsive to determining that a value for a specified field within the given one of the structured data entries matches an item of metadata for the given one of the unstructured clinical notes;
   to determine an initial set of the unstructured clinical notes which satisfy the criteria, wherein the one or more criteria selected such that the one or more criteria are a proxy for the ground truth, and wherein the given one of the unstructured clinical notes is determined to satisfy the criteria based at least in part on the given one of the structured data entries linked thereto;
   to designate at least a portion of the initial set of unstructured clinical notes which satisfy the criteria as a first component of the ground truth, and designating the structured data entries linked to the portion of the initial set of unstructured clinical notes which satisfy the criteria as a second component of the ground truth in response to the determination of the initial set of the unstructured clinical notes that satisfy the one or more criteria;
to use the designated ground truth to train a machine learning model; and
to use the trained machine learning model to perform the natural language processing task.

* * * * *